(12) United States Patent
Dixon

(10) Patent No.: US 8,417,305 B2
(45) Date of Patent: Apr. 9, 2013

(54) NON-INVASIVE MEASUREMENT OF BLOOD OXYGEN SATURATION

(75) Inventor: Barry Dixon, Kew (AU)

(73) Assignee: St. Vincents Hospital (Melbourne) Limited, Fitzroy, Victoria (AU)

( * ) Notice: Subject to any disclaimer, the term of this patent is extended or adjusted under 35 U.S.C. 154(b) by 0 days.

(21) Appl. No.: 12/597,951

(22) PCT Filed: May 2, 2008

(86) PCT No.: PCT/AU2008/000624
§ 371 (c)(1),
(2), (4) Date: Feb. 11, 2010

(87) PCT Pub. No.: WO2008/134813
PCT Pub. Date: Nov. 13, 2008

(65) Prior Publication Data
US 2010/0198027 A1    Aug. 5, 2010

Related U.S. Application Data

(60) Provisional application No. 60/916,108, filed on May 4, 2007.

(30) Foreign Application Priority Data

May 2, 2007   (AU) ................................ 2007902315

(51) Int. Cl.
  *A61B 5/00* (2006.01)
(52) U.S. Cl. ......................... 600/323; 600/328; 600/330
(58) Field of Classification Search .................. 600/323, 600/330, 328
See application file for complete search history.

(56) References Cited

U.S. PATENT DOCUMENTS

| | | | |
|---|---|---|---|
| 5,673,694 A | 10/1997 | Rivers | |
| 5,817,009 A | 10/1998 | Rosenheimer et al. | |
| 6,961,600 B2 | 11/2005 | Kohl et al. | |
| 6,985,763 B2 | 1/2006 | Boas et al. | |
| 7,047,055 B2 | 5/2006 | Boas et al. | |
| 7,072,701 B2 | 7/2006 | Chen et al. | |
| 2002/0038078 A1 | 3/2002 | Ito | |
| 2005/0197551 A1* | 9/2005 | Al-Ali et al. | 600/323 |
| 2005/0197579 A1 | 9/2005 | Baker, Jr. | |
| 2005/0256386 A1 | 11/2005 | Chan et al. | |
| 2006/0253007 A1 | 11/2006 | Cheng et al. | |
| 2007/0112259 A1 | 5/2007 | Tateda et al. | |

FOREIGN PATENT DOCUMENTS

| | | |
|---|---|---|
| EP | 1757224 A2 | 2/2007 |
| WO | WO 96/12435 A2 | 5/1996 |
| WO | WO 00/40147 A1 | 7/2000 |
| WO | WO 03/063697 A1 | 8/2003 |
| WO | WO 2004/054440 A1 | 7/2004 |

* cited by examiner

*Primary Examiner* — Rochelle-Ann J Blackman
(74) *Attorney, Agent, or Firm* — Shay Glenn LLP

(57) ABSTRACT

The invention relates to a method for non-invasive determination of oxygen saturation of blood within a deep vascular structure of a human patient comprising locating on skin of the patient in a vicinity of the deep vascular structure of interest emitter and receiver elements of a light oximeter device, wherein optimal location of said elements is achieved through matching of a plethysmography trace obtained from the oximeter device to known plethysmography characteristics of the deep vascular structure of interest, and wherein oxygen saturation is determined from a ratio of light absorbed at different wavelengths by haemoglobin in the blood within the vascular structure of interest. The invention also relates to modified oximetry devices capable of carrying out the method.

19 Claims, 10 Drawing Sheets

LIJ = 49.344 + .37 * cvc sat; R^2 = .408

THE TRACE INCREASES DURING DIASTOLE AND FALLS DURING SYSTOLE. THIS IS CONSISTENT WITH THE NATURE OF BLOOD FLOW THROUGH THE RIGHT VENTRICLE

SYSTOLE PRECEDES THE FINGER SYSTOLE ON THE PLETHYSMOGRAPHY TRACE. IN ADDITION A DICROTIC NOTCH IS EVIDENT. THESE FEATURES ARE CONSISTENT WITH THE NATURE OF BLOOD FLOW THROUGH THE PULMONARY ARTERY

NON-INVASIVE MEASUREMENT OF BLOOD OXYGEN SATURATION

FIELD OF THE INVENTION

The present invention relates to a method of non-invasively determining oxygen saturation of blood within deep vascular structures, and in particular, but not exclusively, to a method of determining oxygen saturation of central venous, mixed venous and central arterial blood within structures such as the internal jugular vein, superior vena cava, right atrium, right ventricle, pulmonary artery, left atrium, left ventricle, carotid artery and aorta. The invention also relates to devices for use in non-invasively determining oxygen saturation of blood within deep vascular structures.

BACKGROUND OF THE INVENTION

In critically ill and unstable patients assessment of oxygen delivery to the tissues is of vital importance. If inadequate, early interventions to optimise oxygen delivery may prevent multiple organ failure and death[1]. These interventions include administration of intravenous fluids, inotropes (that stimulate heart contraction) and support of ventilation to improve oxygenation of blood.

Central venous or mixed venous blood oxygen saturations reflect the adequacy of oxygen delivery to the parts of the body from which the blood has drained. Mixed venous blood (blood in the right ventricle and central and peripheral parts of the pulmonary arteries) offers the best assessment of the adequacy of oxygen delivery to the whole body. However, central venous blood (blood in the internal jugular, subclavian, femoral and brachiocephalic veins, the inferior and superior vena cava and the right atrium) can be used as a surrogate of the adequacy of oxygen delivery to the whole body.[2]

Currently, assessment of oxygen delivery by venous saturation measurement is generally undertaken by placing a catheter in a central vein or pulmonary artery from which blood is withdrawn. Oxygen saturation of the withdrawn blood is then measured by a blood gas machine. Alternatively, a fibre-optic catheter can be placed in the central vein or pulmonary artery and the oxygen saturation can then be directly measured by optical methods. An approach such as this involving the insertion of an intravenous fibre-optic catheter and direct measurement of oxygen saturation by oximetry is discussed in U.S. Pat. No. 5,673,694 to Rivers.

Both of these approaches involve significant limitations as they require a skilled doctor to insert the catheter, they involve the expense of the blood gas machine or fibre-optic catheter, there is significant risk of adverse events associated with catheter insertion (pneumothorax, infection, bleeding, arrhythmia and tamponade) and finally, there is a delay in obtaining the venous blood saturation while the catheter is inserted.

The present inventor proposes a non-invasive method to directly measure blood oxygen saturation (such as central venous and mixed venous blood oxygen saturation) by placing a light oximeter device on the skin over deep vascular structures. Pulse oximetry, using red and infrared light sources, is an established technique to measure haemoglobin oxygen saturation of blood vessels in the skin. The sensors are commonly placed on fingers, ears, nose and forehead. Pulse oximetry is routinely used in patients to determine whether oxygenation of the blood by the lungs is adequate. Standard pulse oximetry techniques do not provide information about adequacy of oxygen delivery.

Two wavelengths of light are generally used in pulse oximetry one in the red band (between about 620 nm and about 750 nm, but usually in the range of about 640 nm-680 nm, most usually about 660 nm) and the infrared band (between about 750 nm and about 1 mm, but usually between about 900 nm and 960 nm, but often 905 nm, 910 nm or 940 nm). The light is absorbed by haemoglobin in the blood. Deoxyhaemoglobin (Hb) absorbs more of the red band while oxyhaemoglobin absorbs more of the infra-red band. In pulse oximetry light is first transmitted through the tissues and the intensity of the transmitted or reflected light is then measured by the photo-detector. The pulse oximiter determines the AC (pulsatile) component of the absorbance at each wavelength and the amount of the red and infrared AC components is determined, which is indicative of the concentration of oxyhaemoglobin and deoxyhaemoglobin molecules in the blood. The ratio of these molecules indicates the overall haemoglobin oxygen saturation.

The potential of non-invasive trans-cutaneous pulse oximetry to measure the haemoglobin oxygen saturation of blood in deep vascular structures, for example that carry central venous and mixed venous blood, has not previously been recognised. However, a recent patent (U.S. Pat. No. 7,047,055, to Boas and Zourabian[3]) has suggested that light oximetry of deep tissue structures is possible. This work demonstrated a light oximetric technique to measure arterial saturation in the head of a fetus in utero.

Other techniques have been proposed to measure mixed venous oxygen saturation using pulse oximetry. These techniques are, however, invasive and require insertion of an endotracheal tube (U.S. Pat. No. 6,961,600, Kohl)[4] or a transoesophageal echocardiographic probe[5]. Venous saturation of peripheral tissues may also be measured using oximetric techniques. These measurements are, however, of limited clinical utility as they only reflect the extent of oxygen delivery to the peripheral tissue assessed, such as the index finger (US 2005/0256386, Chan) or thenar eminence (U.S. Pat. No. 7,072,701, Chen) (U.S. Pat. No. 6,985,763 Boas).

US patent publication no. 2006/0253007 to Cheng et al describes a light oximetric technique to measure cardiac output, by determining venous blood oxygen saturation in a few deep vascular structures. Cheng et al suggests the concurrent use of ultrasound to assist the correct location of emitter and receiver probes, as well as requiring oximetry measurements be taken simultaneously at two separate locations to distinguish the signal arising from the deep vascular structure from that of surrounding tissue. The present inventor has demonstrated that by utilising the pulsatile nature of the deep vascular structures to generate a plethysmographic trace it is possible to accurately locate the emitter and receiver elements to optimise the signal detected and to thereby do away with the need for concurrent ultrasonography and measurements from more than one location. The individuality of the plethysmography in the present technique is used to identify that the signal is arising from the vascular structure of interest and to filter out signals arising from other interfering chromophores, such as small blood vessels and surrounding tissues.

It is a preferred object of the present invention to overcome or at least ameliorate to some extent problems associated with prior art methods of determining oxygen saturation in deep vascular structures. Other objects of the present invention will become apparent from the following detailed description thereof.

SUMMARY OF THE INVENTION

According to one embodiment of the present invention there is provided a method for non-invasive determination of oxygen saturation of blood within a deep vascular structure of a human patient comprising locating on skin of the patient in a vicinity of the deep vascular structure of interest emitter and receiver elements of a light oximeter device, wherein optimal location of said elements is achieved through matching of a plethysmography trace obtained to known plethysmography characteristics of the deep vascular structure of interest, and wherein oxygen saturation is determined from a ratio of light absorbed at different wavelengths by haemoglobin in the blood within the vascular structure of interest.

In a preferred embodiment the deep vascular structure of interest is selected from the internal jugular vein, subclavian vein, femoral vein, brachiocephalic vein, inferior vena cava, superior vena cava, right atrium, right ventricle, pulmonary artery (including both peripheral and central parts), left atrium, left ventricle, carotid artery, vertebral artery, subclavian artery, brachiocephalic artery, femoral artery and aorta.

In one embodiment the method is for non-invasive determination of central venous blood oxygen saturation. In this case the deep vascular structure of interest is preferably selected from the internal jugular vein, subclavian vein, femoral vein, brachiocephalic vein, inferior vena cava, superior vena cava and right atrium.

In another preferred embodiment the method is for non-invasive determination of mixed venous blood oxygen saturation. In this case the deep vascular structure of interest is preferably selected from the right ventricle and pulmonary artery.

In another preferred embodiment the method is for non-invasive determination of central arterial oxygen saturation. In this case the deep vascular structure of interest is preferably selected from the left atrium, left ventricle, carotid artery, vertebral artery, subclavian artery, brachiocephalic artery, femoral artery and aorta.

Preferably the emitter element emits light in both red and infra-red wavelengths. Preferably the red light has a wavelength of between about 620 nm and about 750 nm, more preferably between about 640 nm and about 680 nm and most preferably the red light has a wavelength of about 660 nm.

Preferably the infra-red light has a wavelength of between about 750 nm and about 1 mm. More preferably the infra-red light has a wavelength of between about 900 nm and about 960 nm and most preferably the infra-red light has a wavelength of about 905 nm, 910 nm or 940 nm.

According to another embodiment of the present invention there is provided an oximetry device for use in the method as outlined above.

According to another embodiment of the present invention there is provided an oximetry device comprising a central processing unit, a display and emitter and receiver elements adapted for releasable application to human skin, all of which are workably connected in use; the emitter elements being equipped to emit light of both red and infra-red wavelengths and the receiver elements adapted to detect said light, with information relating to levels of emitted and received light being transmitted to said central processing unit; said central processing unit being capable of matching plethysmography characteristics derived from the information relating to levels of emitted and received light with known plethysmography characteristics of a deep vascular structure of interest, to ensure optimal location in use of the emitter and receiver elements on the skin in a vicinity of the deep vascular structure of interest; said central processing unit also being capable of deriving from the information relating to levels of emitted and received light a measurement of blood oxygen saturation within the deep vascular structure of interest, which can be made available on the display.

Preferably the plethysmography characteristics of the deep vascular structure of interest can also be made available on the display.

The workable connection can be either physical or wireless.

Preferably the red light has a wavelength of between about 620 nm and about 750 nm, more preferably between about 640 nm and about 680 nm and most preferably the red light has a wavelength of about 660 nm.

Preferably the infra-red light has a wavelength of between about 750 nm and about 1 mm. More preferably the infra-red light has a wavelength of between about 900 nm and about 960 nm and most preferably the infra-red light has a wavelength of about 905 nm, 910 nm or 940 nm.

BRIEF DESCRIPTION OF THE FIGURES

The invention will be further described with reference to the figures, wherein.

DETAILED DESCRIPTION OF THE INVENTION

Figure 1:
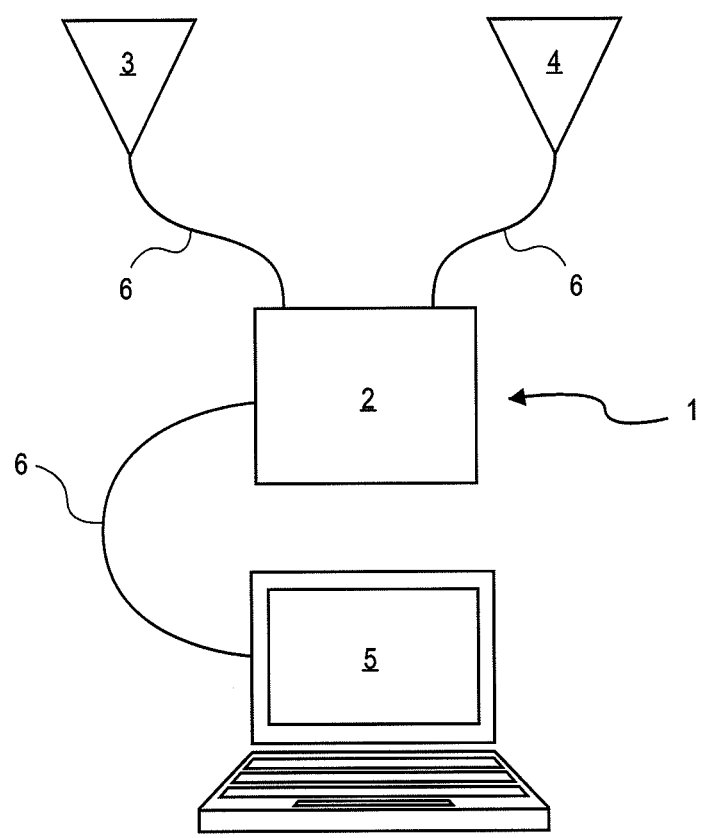
FIG. 1 is a schematic diagram of the device of the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that that prior art forms part of the common general knowledge in Australia.

Reference within this specification to prior patent documents or technical publications is intended to constitute an inclusion of the subject matter of such prior publications within the present specification in their entirety, by way of reference.

To assist in understanding of this document definitions of a few important terms are provided below:

Central venous blood is (relatively de-oxygenated) blood located within centrally (rather than peripherally) located veins. It includes blood within the internal jugular, subclavian, femoral and brachiocephalic veins, the inferior and superior vena cava and the right atrium.

Mixed venous blood is (relatively de-oxygenated blood) located within the right ventricle and central and peripheral parts of the pulmonary arteries, which is being returned to the lungs for re-oxygenation. Monitoring of oxygen saturation in mixed venous blood provides the best assessment of the adequacy oxygen delivery.

Central arterial blood is oxygenated blood within centrally (rather than peripherally) located arteries, other than the pulmonary artery (which carries de-oxygenated blood). It includes blood within the left atrium, left ventricle and carotid, vertebral, subclavian, brachiocephalic, femoral and aortic arteries.

Deep vascular structures are major blood vessels (including the chambers of the heart) which are not superficially located. That is, they are generally at least 1 cm, usually at least 2 cm and most usually at least 3 cm to 5 cm, and up to about 10 cm beneath the skin of normal patients, depending upon the size and anatomy of the patient concerned. Deep vascular structures include the internal jugular, subclavian, femoral and brachiocephalic veins and the inferior and superior vena cava, the right atrium, right ventricle and central and peripheral parts of the pulmonary arteries, the left atrium, left ventricle and carotid, vertebral, subclavian, brachiocephalic, femoral and aortic arteries.

A Plethysmography trace is the pulsatile signal arising from blood vessels and other blood containing structures, obtained by traditional pulse oximetry methods. The plethysmography trace reflects changes in blood volume and red blood cell orientation through the pulsatile cycle as well as other physical characteristics of the blood vessel or blood containing structure. These factors influence the extent of absorption of oximetry light. The nature of the plethysmography trace for a particular pulsatile vascular structure is therefore a distinguishing feature of that structure.

The present invention relates generally to methods and devices for determining blood oxygen saturation in deep vascular structures, which do not require the use of ultrasound to locate the vascular structure of interest and also do not require the taking of oximetry measurements at multiple locations. This is achieved by exploiting traditional oximetry techniques and devices, but in conjunction with using the plethysmography trace obtained to optimally locate the emitter and receiver elements of the device on the skin in the vicinity of the structure of interest. By using this approach it is also possible to filter out signals obtained from other chromophores such as those located in surrounding tissues or smaller vessels.

The methods and device of the invention are useful in a number of clinical settings. Firstly, to measure the central venous blood and mixed venous blood oxygen saturations. This allows the adequacy of oxygen delivery to the tissues throughout the body to be assessed non-invasively. Secondly, to measure the oxygen saturation of blood draining from a particular part of the body, such as the brain, by monitoring blood saturations of the internal jugular veins. This allows the adequacy of oxygen delivery to that region of the body to be assessed non-invasively. A further application is to measure the central arterial blood oxygen saturation. This allows arterial oxygen saturations to be monitored in conditions in which blood flow to superficial tissues, such as the skin, may be poor such that no reliable signal can be obtained by traditional pulse oximetry methods.

It is therefore possible using the methods and devices of the invention to assess the adequacy of oxygen delivery to the whole body of a human or animal patient, which will be of importance for example in monitoring critically ill or potentially unstable patients, monitoring before, during and after surgical procedures, monitoring during and after cardiac arrest, monitoring during exercise or in cardiac stress testing to detect cardiac or respiratory dysfunction, in exercise testing in humans or animals to document the workload at which the anaerobic threshold is reached and in self monitoring of cardiac function by athletes and high altitude climbers, pilots of non-pressurised aircraft and others exposed to low oxygen environments.

The invention also allows an assessment of the adequacy of oxygen delivery to the brain, through monitoring of oxygen saturation in one or both of the internal jugular veins. This application is indicated in patients in which blood flow to the brain may be inadequate, such as any form of acute brain injury, following neurosurgical procedures, following operations or procedures on blood vessels supplying the brain, such as the aorta, carotid, vertebral, cerebella and cerebral arteries.

In addition to measurement of central venous and mixed venous blood oxygen saturation, this trans-cutaneous technique can be used to measure central arterial blood oxygen saturation. In some clinical situations it is difficult to obtain a superficial pulse oximetry trace due to poor blood flow to the peripheral tissues[6]. These situations include low cardiac output (such as in cardiac arrest, shock), sepsis (resulting in peripheral shut down of blood flow), peripheral vascular disease and exposure to a cold environment. In such situations measurement of central arterial blood oxygen saturation using the present invention will offer a valuable aid to patient management. This technique allows measurement of blood oxygen saturation in central deep vascular structures containing arterial blood, such as the left atrium, left ventricle and carotid, vertebral, subclavian, brachiocephalic, femoral and aortic arteries.

An important feature of the present invention relates to reliance on the plethsymographic character of the vascular structure of interest detected by the oximetry technique. The pulsatile signal (or plethysmograph trace) of a vascular structure reflects the temporal changes in blood flow through the deep vascular structure of interest. As the blood flow through the deep vascular structures has characteristic features, the plethysmograph trace also reflects these characteristic features and can therefore be used to identify that the signal is arising from the particular deep vascular structure of interest. The characteristic features of a plethysmography trace from a particular deep vascular structure can therefore also be used to filter out other pulsatile signals arising from other interfering chromophores, such as small blood vessels in surrounding tissues. These contribution of these other interfering pulsatile signals can also be assessed through conventional pulse oximetry.

Another aspect of the invention that enables oximetry to be used to monitor blood oxygen saturation in deep vascular structures, where this had not been considered possible in the past, relates to the relative high volume of blood in deep large blood vessels that results in relatively high absorption of light compared to the blood volume in small blood vessels of the skin and surrounding tissues. This difference in blood volume provides a further means of effectively filtering out signals arising from interfering chromophores, such as small blood vessels in surrounding tissues.

The present invention allows for the determination of blood oxygen saturation in deep vascular structures in a non-invasive manner. By this it is meant that there is no need for direct sampling of blood and nor is it necessary for any form of central line or other probe to be inserted within the patient, either within or adjacent to vascular structures (such as within the gastrointestinal tract in the vicinity of a vascular structure). Indeed, the present invention can conveniently be conducted by placing the emitter and receiver elements of a light oximeter device on the skin of the patient over deep vascular structure of interest.

Deep vascular structures within which blood oxygen saturation can be determined include those containing central venous blood, such as the internal jugular vein, subclavian vein, femoral vein, brachiocephalic vein, inferior vena cava, superior vena cava and right atrium, those containing mixed venous blood, such as the right ventricle and pulmonary artery (central and peripheral regions) and those containing central arterial blood, such as the left atrium, left ventricle, carotid artery, vertebral artery, subclavian artery, brachiocephalic artery, femoral artery and aorta.

The right ventricle has a number of characteristics that make it well suited for monitoring. Firstly, it is a pulsatile chamber of the heart; hence the light absorbance will vary with the cardiac cycle. Peak absorbance occurs during diastole (the point in the cardiac cycle when the right ventricle fills with blood). This characteristic provides a method to filter out absorbance by arterial and venous blood in superficial tissues and by non-pulsatile chromophores such as the skin and muscle. Secondly, the right ventricle at the end of diastole is a significant absorber of light—at this point in the cardiac cycle it contains around 100-200 ml of blood. This exceeds the volume of blood in the overlying tissues (through which the light also passes) by at least a factor of 10. The ratio of relative absorbance of the two wavelengths of light during right ventricular diastole, can then be used to derive the oxygen saturation of blood in the right ventricle.

In conducting the methods of the present invention it is possible to utilise modified conventional pulse oximetry devices, such as for example those described in the book Pulse Oximetry by John T B Moyle[7], the disclosures of which are included herein in their entirety by way of reference. To work optimally a number of modifications are preferred. Modifications that can optimise the signal include utilisation of lasers rather than light emitting diodes to provide the light sources, increasing the distance between the light emitter and light receiving sensors, utilising the plethysmograph trace to identify the signal is arising from the deep vascular structure of interest, utilising the plethysmography trace to filter out signals arising from other interfering chromophores, utilising the signal arising from the relatively high volume of blood in the deep vascular structures (in relation to small blood vessels in superficial tissues) to filter out signals arising from small superficial blood vessels that may act as interfering chromophores, re-calibration of the absorption signals to improve accuracy of oximetry of de-oxygenated rather than traditional oxygenated blood and modification of the formula used to estimate the photon path length to reflect the photon path length required to reach deep vascular structures.

Figure 2:
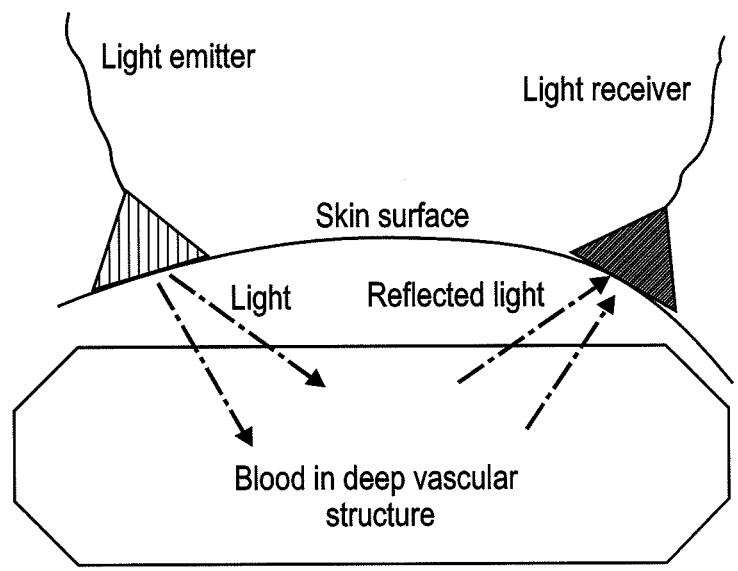
FIG. 2 is a schematic diagram of the light emitter and receiver elements of the device of the invention when in position on the skin of a patient in the vicinity of a deep vascular structure of interest.

As shown in FIG. 1 devices (1) specifically useful in the present invention have a number of basic components, such as a central processing unit (2), a display (5) (for in some manner reporting plethysmographic and/or oxygen saturation information) and emitter (3) and receiver (4) elements that respectively emit and sense red and infra-red light. The display (5) may for example take the form of a printer that produces a paper scan of oxygen saturation and plethysmographic trace, a video type screen (such as cathode ray, plasma, liquid crystal) or even a device that produces an audible output of the necessary information. Naturally, in use the various components of the device (1) are connected either physically such as by wires (6) or fibre-optic cable or using conventional wireless technologies. The central processing unit (2) receives from the emitter (3) and receiver (4) elements information regarding the emitted and received light, from which it is able to match the plethysmographic character of the body being monitored with the known plethysmographic character of the deep vascular structure of interest, and is able to compute oxygen saturation from the information on emitted and received light transmitted to it, for example by utilising a clinically derived relationship for oxygen saturation in the particular structure of interest for a particular class or group of patients, as referred to further below. By matching the plethysmographic character against an ideal and giving an operator feedback via the display (5) on this the operator is able to ensure the optimal location of the emitter (3) and receiver (4) elements in the vicinity of the structure of interest (that is on the skin in the region of the structure that allows penetration of light between the emitter/receiver element and the blood within the structure of interest), as schematically depicted in FIG. 2.

In one embodiment an optical fibre is used to deliver a probe light beam (the emitter) combined from a pair of remote sources to a fitting placed in contact with the skin above, for example, the right ventricle of the patient. The fitting also contains a second optical fibre that is used to collect reflected light (the detector) from the internal tissues and blood. The optical fibres are provided with suitable collimation optics to direct the delivered beam and selectively collect the reflected light along preferred directions. The optical fibers will preferably have an adjustable mount so that the delivery and sampling directions can be modified to match different patient morphologies, to thereby meet the requirements of different patient chest size, shape, bone structure, muscle and fat content. The reflected light is spectrally analysed and converted to an electrical signal by a photodetector. Optimal light delivery and collection geometries, light sources and photodetector types can be adjusted to give optimal results. Signals from sources other than the vascular structure of interest are removed by a combination of spatial filtering, mathematical processing and computer analysis algorithms.

Two wavelengths of light are generally used in pulse oximetry one in the red band (between about 620 nm and about 750 nm, but usually in the range of about 640 nm-680 nm, most usually about 660 nm) and one in the infrared band (between about 750 nm and about 1 mm, but usually between about 900 nm and 960 nm, but often 905 nm, 910 nm or 940 nm). The light is absorbed by haemoglobin in the blood. Deoxyhaemoglobin (Hb) absorbs more of the red band while oxyhaemoglobin absorbs more of the infra-red band. In pulse oximetry light is first transmitted through the tissues and the intensity of the transmitted (reflected) light is then measured by the photo-detector. The pulse oximiter determines the AC (pulsatile) component of the absorbance at each wavelength and the amount of the red and infrared AC components is determined, which is indicative of the concentration of oxyhaemoglobin and deoxyhaemoglobin molecules in the blood. The ratio of these molecules indicates the overall haemoglobin oxygen saturation.

Figure 3A:
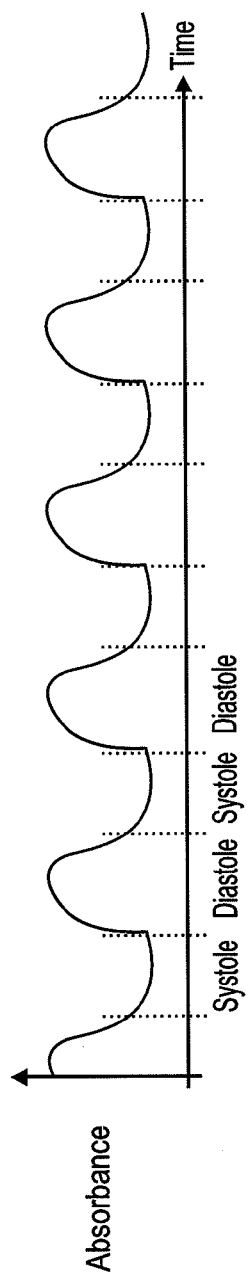
FIG. 3 shows a scan of relative light absorbance against time for oximetry of the right ventricle, demonstrating in (a) the phases of right ventricle emptying (systole) and filling (diastole) and the peak in relative absorbance during diastole. In (b) the higher relative absorbance of red light is shown in the case where the blood has a lower oxygen saturation level and in (c) the lower relative absorbance of infra-red light is shown in the case where the blood has a lower oxygen saturation level.
Figure 3B:
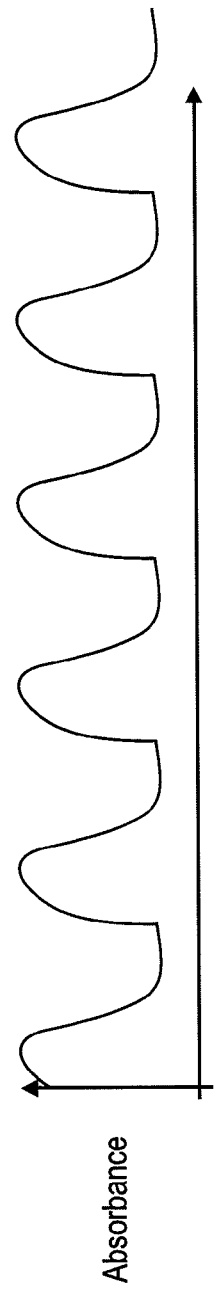
Figure 3C:
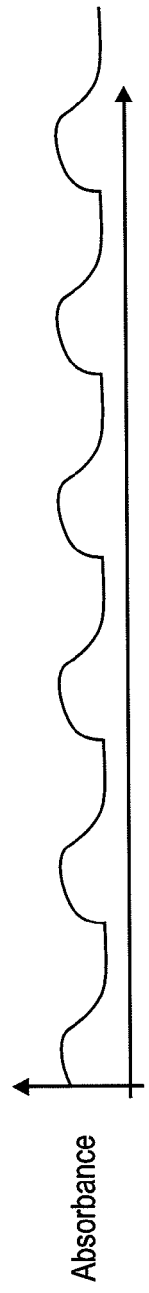
Figure 4:
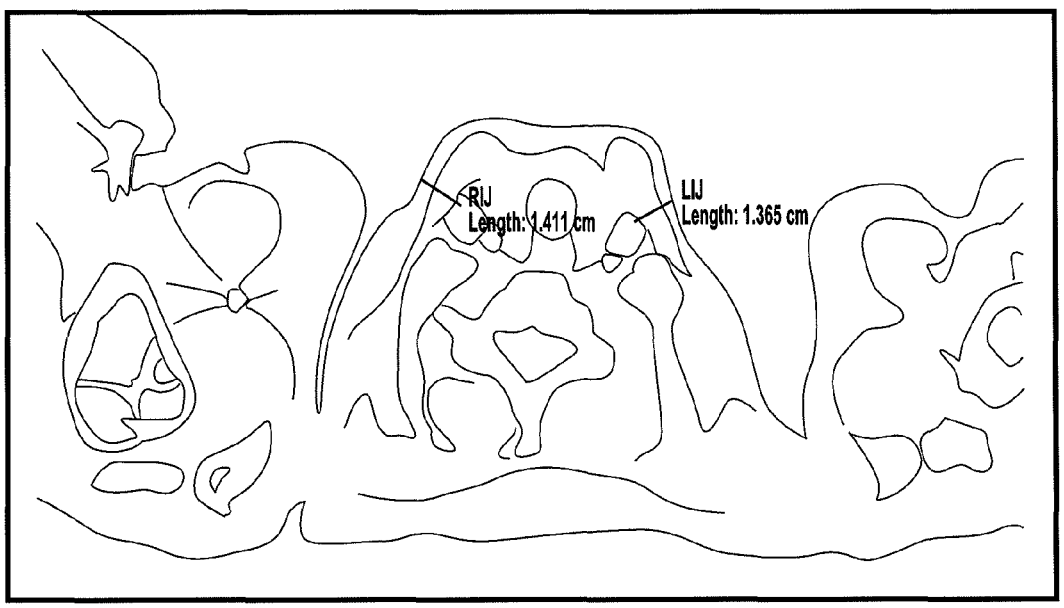
FIG. 4 is a CT scan demonstrating the distance between the skin and the internal jugular veins and carotid arteries (where "RIJ" is the right internal jugular vein and "LIJ" is the left internal jugular vein).
Figure 5:
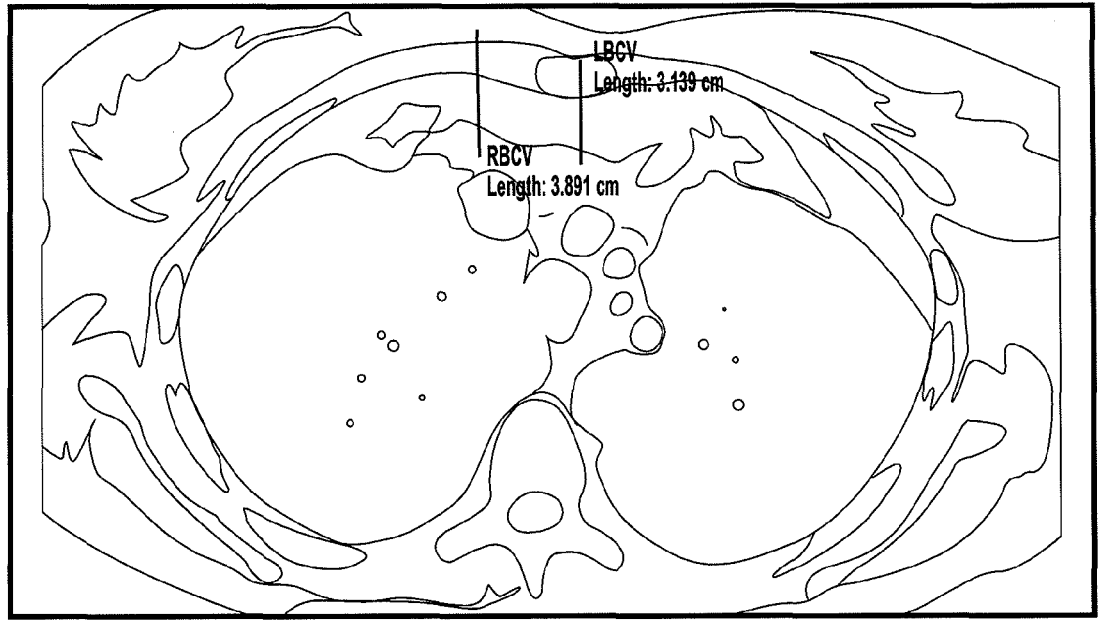
FIG. 5 is a CT scan demonstrating the distance between the skin and the brachiocephalic veins (where "LBCV" is the left brachiocephalic vein and "RBCV" is the right brachiocephalic vein).
Figure 6:
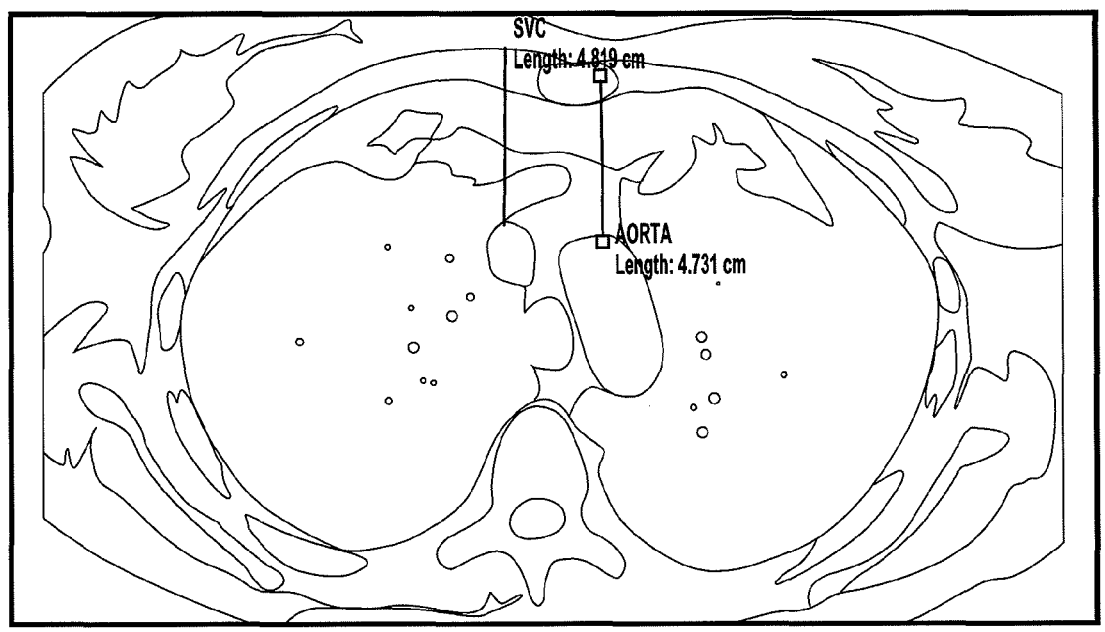
FIG. 6 is a CT scan demonstrating the distance between the skin and the aorta and superior vena cava (where "SVC" is the superior vena cava).
Figure 7:
FIG. 7 is a CT scan demonstrating the distance between the skin and the pulmonary artery (where "PA" is the pulmonary artery).
Figure 8:
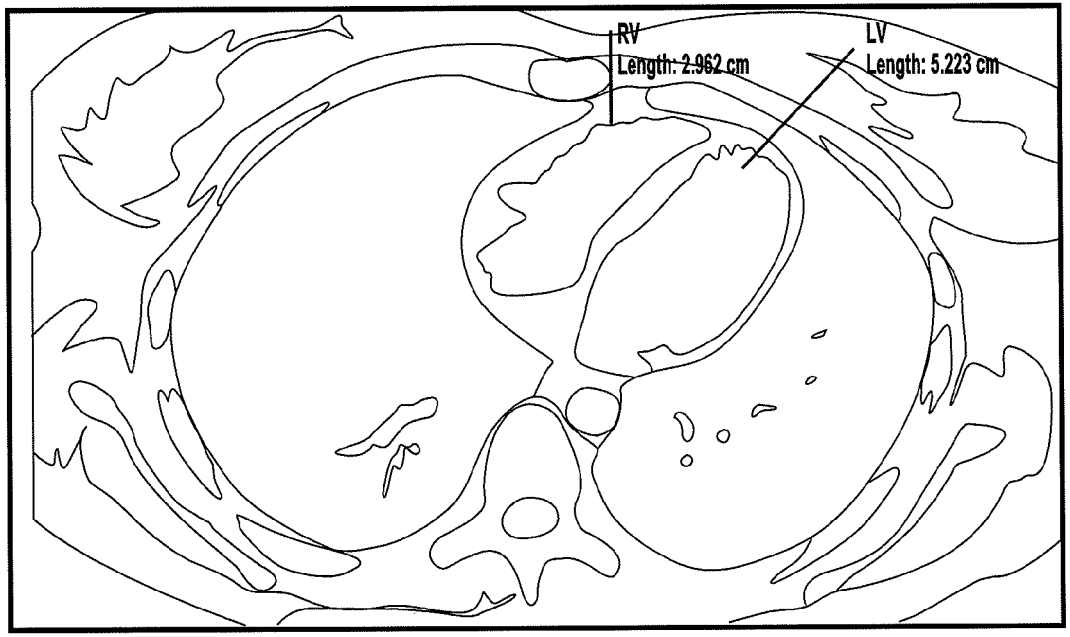
FIG. 8 is a CT scan demonstrating the distance between the skin and the right and left ventricles (where "RV" is the right ventricle and "LV" is the left ventricle).

The principle of operation of the present methods are graphically represented in FIG. 3. As can be seen in FIG. 3(a) relative light absorbance in the vascular structure (in this case the right ventricle) increases as the right ventricle fills with blood during diastole. FIG. 3(b) shows that relative absorbance of red light is higher when the blood in the vascular structure has lower oxygen saturation and FIG. 3(c) shows that relative absorbance of infra-red light is lower when the blood in the vascular structure has lower oxygen saturation. The ratio of absorbance of two or more wavelengths of light, particularly in the case of the right ventricle during diastole, is used to derive the oxygen saturation of the blood within the vascular structure. FIG. 3 also demonstrates the plethysmographic character that is particular to the right ventricle, and which is used to discriminate between the signal derived from the right ventricle and from other vascular structures to thereby optimally position the emitter and detector elements.

In the case of the use of pulse oximetry in the methods of the present invention to determine blood oxygen saturation levels within deep vascular structures clinical studies can be conducted on a patient population to determine the relationship between the apparent oxygen saturation determined by pulse oximetry for the deep vascular structure and the actual oxygen saturation in the vessel as determined by an analytical method (e.g. by use of a blood oxygen analyser). In view of this knowledge the device can be calibrated and accurate quantification of the oxygen saturation in a particular deep vessel for a particular patient can be obtained non-invasively. In determining the appropriate calibration it is be useful to take into account not only the deep vascular structure of interest, but also the age, height, weight and/or general medical condition of the patient. In this way the relationship relied upon can be specific for the structure of interest in patients of similar stature and condition.

The present invention will now be described further with reference to the following non-limiting examples.

EXAMPLE 1

Determination of Blood Oxygen Saturation in Deep Vascular Structures of Human Patients A non-invasive method to assess oxygen saturation of blood in central veins and mixed venous blood in the right ventricle or pulmonary artery could have great clinical utility in documenting the adequacy of oxygen delivery in potentially unstable and critically ill patients.

Previous studies have shown light can penetrate a number of centimeters into body tissues[3]. There has, however, been no previous demonstration that oximetry techniques can be used to reliably obtain oxygen saturation readings from blood in deep vascular structures. The present inventor investigated a novel non-invasive transcutaneous method to measure central venous, mixed venous and central arterial blood oxygen saturations by placing a light oximeter device on the skin over large blood vessels and cardiac chambers carrying these types of blood.

Methods

The distance in centimeters between the skin and deep vascular structures on a series of computed tomography (CT) scans of 6 supine patients was assessed.

Results

The following average distances (cm) between the skin surface and underlying deep vascular structures were determined from analysis of the CT scans;
  Pulmonary artery 4.3±1.0 (mean and standard deviation)
  Right ventricle 3.5±0.8
  Left ventricle 4.0±1.3
  Right atrium 5.9±1.5
  Left brachiocephalic vein 4.0±1.0
  Superior vena cava 6.2±1.5
  Right brachiocephalic vein 4.5±1.6
  Right brachiocephalic artery 4.8±2.1
  The carotid arteries and internal jugular veins were always less than 3 cm from the skin surface.
  Example CT scans are shown in FIGS. 4 to 8.

Discussion

It was demonstrated that deep vascular structures in the neck and the chest lie less than 7 cm from the skin surface.

EXAMPLE 2

Character of Plethysmography Trace and Blood Oxygen Saturation Level

Methods

A clinical study was undertaken in 8 critically ill ventilated patients. All patients had a central line placed in the superior vena cava. Transcutaneous pulse oximetry according to the invention was used to assess the oxygen saturation of venous blood passing through deep vascular structures including the internal jugular vein, the right ventricle and pulmonary artery. The saturation of blood in central arterial vascular structures including the aorta and left ventricle was also assessed.

The light emitter and light receiver elements of a pulse oximeter device (OxiMax adult oxygen sensor by Nellcor attached to a pulse oximiter module of a Hewlett Packard Critical Care Monitor) were placed 2 to 8 cm apart on the skin over the vascular structure of interest.

The inventor also investigated whether the plethysmography trace obtained was consistent with the signal arising from the deep vascular structure of interest. The pulsatile nature of blood flow through each of the deep vascular structures has certain characteristics peculiar to each. The inventor hypothesised that the plethysmography trace would reflect these characteristics.

The plethysmography trace and blood oxygen saturation were documented. In patients in whom a reasonable plethysmography trace was obtained superior vena cava blood was analysed in a blood gas machine to determine the oxygen saturation In such patients example plethysmography traces were also obtained.

Results

Figure 9:
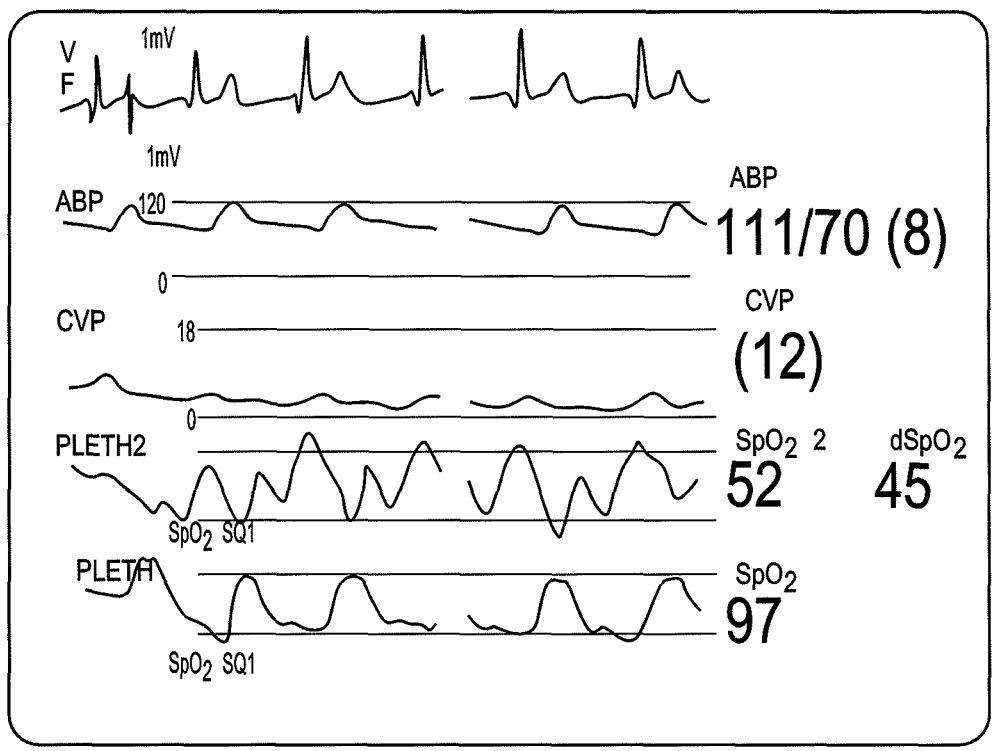
FIG. 9 shows (from top to bottom) the electrocardiogram (ECG), arterial blood pressure, central venous pressure, right internal jugular vein and finger plethysmography traces from one of the patients in the clinical study.

In the internal jugular vein the inventor determined the plethysmograph trace to be consistent with the expected signal arising from the internal jugular vein in 5 of the 8 patients studied. The plethysmograph trace from these 5 patients demonstrated the characteristic "a" and "v" waves of the central venous pressure trace (FIG. 9). The oxygen saturation level was low and was consistent with the level expected from blood in a central vein.

Figure 10:
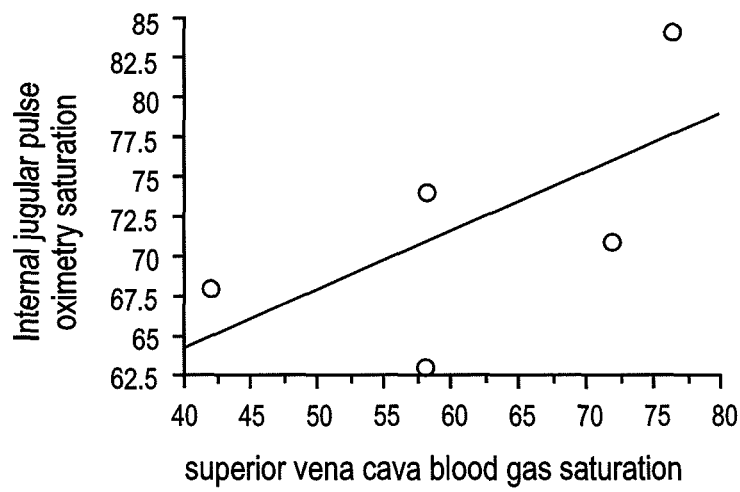
FIG. 10 shows a regression plot of internal jugular vein pulse oximetry determined oxygen saturation against superior vena cava blood gas determined oxygen saturation.

For the 5 patients in whom a reliable internal jugular vein plethysmograph trace was obtained blood was aspirated from the central line in the superior vena cava and blood gas saturations were measured. A linear relationship between the pulse oximeter and blood gas determined oxygen saturations (FIG. 10) was identified. The correlation coefficient ($R^2$) was 0.4.

Figure 11:
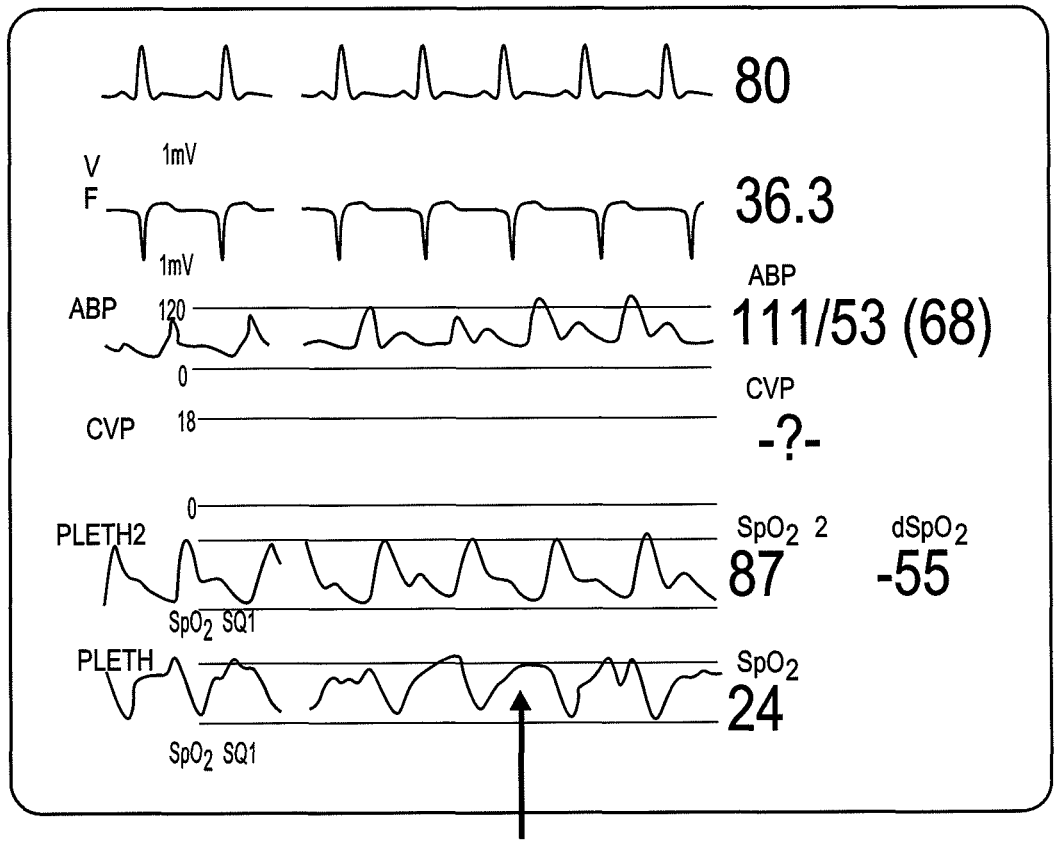
FIG. 11 shows (from top to bottom) the ECG, arterial blood pressure and finger and right ventricular plethysmography traces from one of the patients in the clinical study.

The plethysmograph trace was consistent with the signal arising from the right ventricle in 2 of the 8 patients studied. During diastole the signal increased, this is consistent with diastolic filling of the right ventricle with blood. During systole the signal decreased, this is consistent with emptying of the ventricle of blood (FIG. 11). The signal was, therefore, the inverse of the finger plethysmography trace. In addition the saturation level was low and therefore consistent with the signal arising from mixed venous blood (average value was 45%).

Figure 12:
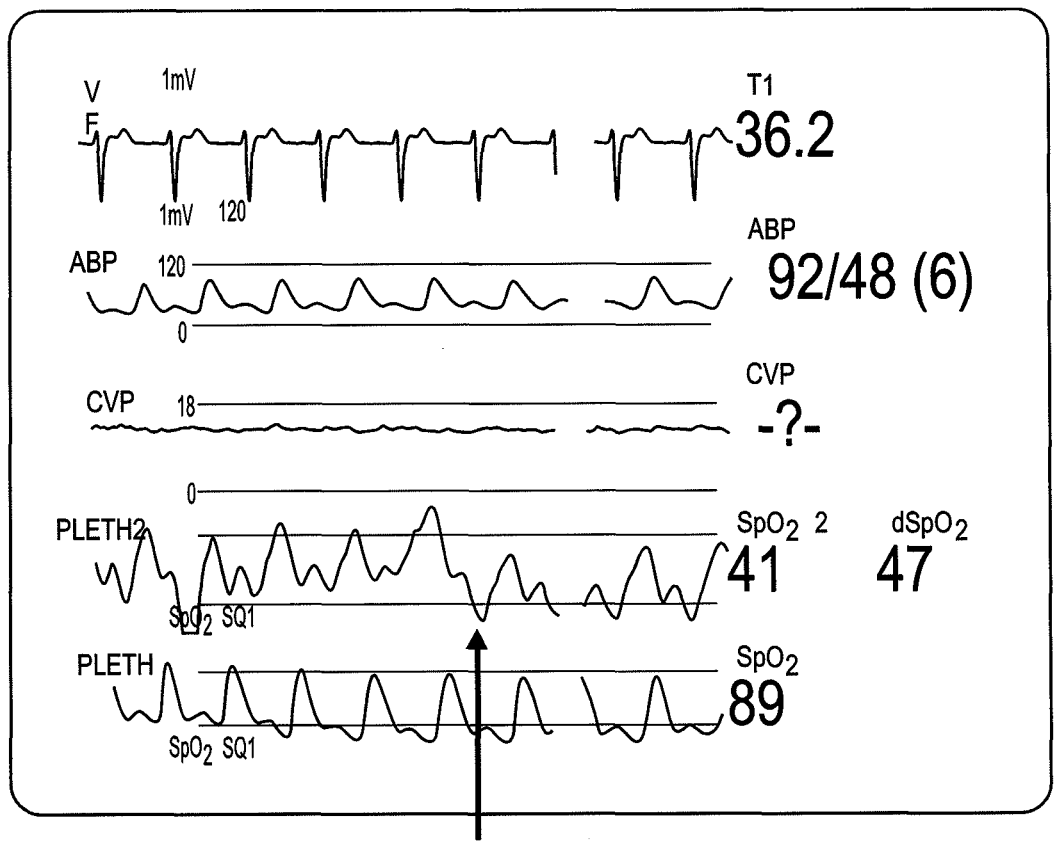
FIG. 12 shows (from top to bottom) the ECG, arterial blood pressure, central venous pressure and pulmonary artery and finger plethysmography traces from one of the patients in the clinical study

The plethysmography trace was consistent with the signal arising from blood in the pulmonary artery in 2 of the 8 patients studied. The systolic wave preceded the finger systolic wave (consistent with a central vascular source of the signal). In addition a dicrotic notch was evident (FIG. 12). Finally, the oxygen saturation level was low and therefore consistent with the signal arising from mixed venous blood (55%)

Figure 13:
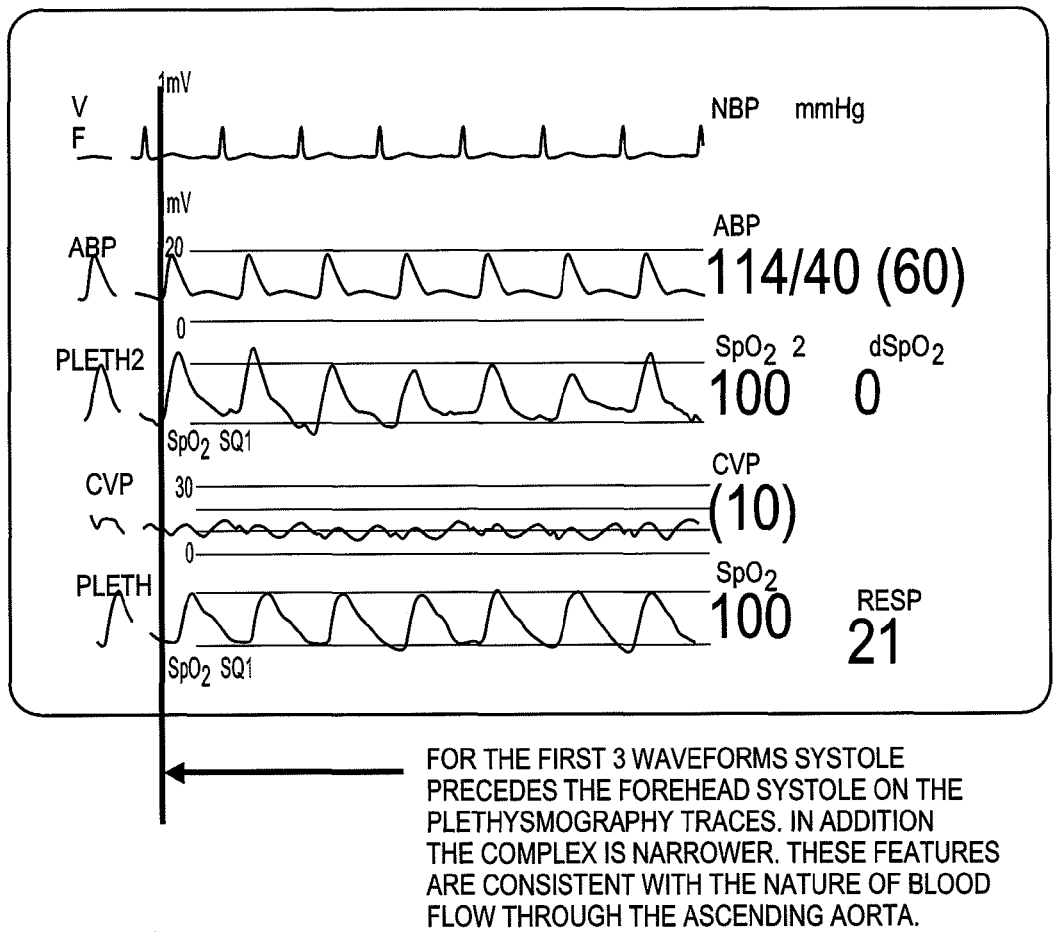
FIG. 13 shows (from top to bottom) the ECG, arterial blood pressure, aortic plethysmography trace, central venous pressure and pulmonary artery and forehead plethysmography trace from one of the patients in the clinical study

The plethysmography trace was consistent with the signal arising from blood in the ascending aorta in 4 of the 8 patients studied. The systolic wave preceded the forehead systolic wave (consistent with a central arterial source of the signal). In addition the waveform was narrower (FIG. 13).

Discussion

It was shown that light can reach deep vascular structures and the returning signal can be used to obtain a measure of the blood oxygen saturation within the structure of interest.

A linear relationship was also demonstrated between the internal jugular vein pulse oximetry and superior vena cava blood gas saturation levels, indicating that with calibration accurate quantification of oxygen saturation in the deep vascular structures can be obtained.

At least in some patients the nature of the plethysmography trace reflected the temporal changes in blood flow through these deep vascular structures. The character of the trace was therefore peculiar to each of these deep vascular structures. The distinctiveness of the plethysmography trace for each structure can therefore be used to identify that the signal is arsing from the appropriate deep vascular structure (and to thereby enable optimal location of the emitter and receiver elements in the vicinity of the structure of interest), and can also be used to filter out signals arising from other interfering chromophores, such as those in small blood vessels and other surrounding tissues.

REFERENCES

1 Rivers E, Nguyen B, et al. Early goal-directed therapy in the treatment of severe sepsis and septic shock. N Engl J Med 2001; 345:1368-1377
2 Marx G, Reinhart K. Venous oximetry. Curr Opin Crit Care 2006; 12:263-268
3 Vintzileos A M, Nioka S, et al, Transabdominal fetal pulse oximetry with near-infrared spectroscopy. Am J Obstet Gynecol 2005; 192:129-133
4 Wei W, Zhu Z, et al. A pilot study of continuous transtracheal mixed venous oxygen saturation monitoring. Anesth Analg 2005; 101:440-443, table of contents
5 Margreiter J, Keller C, et al. The feasibility of transesophageal echocardiograph-guided right and left ventricular oximetry in hemodynamically stable patients undergoing coronary artery bypass grafting. Anesth Analg 2002; 94:794-798, table of contents
6 Keller C, Brimacombe J, et al. A pilot study of pharyngeal pulse oximetry with the laryngeal mask airway: a comparison with finger oximetry and arterial saturation measurements in healthy anesthetized patients. Anesth Analg 2000; 90:440-444
7. Pulse Oximetry (Second Edition). John T B Moyle. BMJ Books 2002, BMA House, London.

The invention claimed is:

1. A method for non-invasive determination of oxygen saturation of central venous or mixed venous blood within a deep vascular structure of interest in a human patient that contains central venous or mixed venous blood, the method comprising:
    placing emitter and receiver elements of a light oximeter device on the patient's skin in the vicinity of the deep vascular structure of interest wherein the deep vascular structure contains central venous or mixed venous blood, further wherein placement of said elements is achieved through matching of a plethysmography trace obtained from the oximeter device to known plethysmography characteristics of the deep vascular structure of interest; and
    determining oxygen saturation of blood within the deep vascular structure of interest, wherein oxygen saturation is determined from a ratio of light absorbed at different wavelengths by haemoglobin in the blood within the deep vascular structure of interest.

2. The method of claim 1 wherein the step of determining oxygen saturation comprises determining central venous blood oxygen saturation.

3. The method of claim 2 wherein the deep vascular structure of interest is selected from the internal jugular vein, subclavian vein, femoral vein, brachiocephalic vein, inferior vena cava, superior vena cava and right atrium.

4. The method of claim 1 wherein the step of determining oxygen saturation comprises determining mixed venous blood oxygen saturation.

5. The method of claim 4 wherein the deep vascular structure of interest is selected from the right ventricle and pulmonary artery.

6. The method of claim 1 further comprising emitting light from the emitter element in both red and infra-red wavelengths.

7. The method of claim 6 wherein the red light has a wavelength of between about 620 nm and about 750 nm.

8. The method of claim 6 wherein the red light has a wavelength of between about 640 nm and about 680 nm.

9. The method of claim 6 wherein the red light has a wavelength of about 660 nm.

10. The method of claim 6 wherein the infra-red light has a wavelength of between about 750 nm and about 1 mm.

11. The method of claim 6 wherein the infra-red light has a wavelength of between about 900 nm and about 960 nm.

12. The method of claim 6 wherein the infra-red light has a wavelength of about 905 nm, 910 nm or 940 nm.

13. An oximetry device configured for use in the method of claim 1.

14. An oximetry device comprising:
    a central processing unit, a display; and emitter and receiver elements adapted for releasable application to human skin, wherein the emitter elements are configured to emit light of both red and infra-red wavelengths and the receiver elements are configured to detect said light, and to transmit information relating to levels of emitted and received light to said central processing unit;

wherein said central processing unit is configured to match plethysmography characteristics derived from the transmitted information relating to levels of emitted and received light with predetermined plethysmography characteristics of a deep vascular structure of interest that contains central venous or mixed venous blood, to ensure positioning of the emitter and receiver elements on the skin in a vicinity of the deep vascular structure of interest; said central processing unit also being configured to derive a measurement of blood oxygen saturation within the deep vascular structure of interest from the information relating to levels of emitted and received light, for display;

wherein the central processing unit, display and emitter and receiver elements are workably connected in use.

15. The oximetry device according to claim 14 wherein the device is configured so that the plethysmography characteristics of the deep vascular structure of interest can be made available on the display.

16. The oximetry device of claim 14 wherein the workable connection is physical.

17. The oximetry device of claim 14 wherein the workable connection is wireless.

18. The oximetry device of claim 14 wherein the emitter elements are configured to emit red light at a wavelength of between about 640 nm and about 680 nm.

19. The oximetry device of claim 14 wherein the emitter elements are configured to emit infra-red light at a wavelength of between about 900 nm and about 960 nm.

* * * * *